United States Patent [19]

Topp-Jorgensen

[11] Patent Number: 4,536,485

[45] Date of Patent: Aug. 20, 1985

[54] PROCESS FOR THE PREPARATION OF CATALYSTS FOR USE IN ETHER SYNTHESIS

[75] Inventor: Jorgen Topp-Jorgensen, Hvidovre, Denmark

[73] Assignee: Haldor Topsoe A/S, Denmark

[21] Appl. No.: 690,335

[22] Filed: Jan. 10, 1985

[30] Foreign Application Priority Data

Jan. 10, 1984 [DK] Denmark ................................. 95/84

[51] Int. Cl.$^3$ ........................ B01J 29/08; B01J 29/28; B01J 21/16
[52] U.S. Cl. ..................................... 502/62; 502/77; 502/80; 502/79; 502/86
[58] Field of Search ...................... 502/62, 77, 79, 80, 502/86

[56] References Cited

U.S. PATENT DOCUMENTS 3,329,730  7/1967  Vives ............................... 502/80 X
3,336,240  8/1967  Erickson et al. ................... 502/80
3,853,743  12/1974  Schwartz ........................ 502/77 X

FOREIGN PATENT DOCUMENTS 957946  9/1982  U.S.S.R. ................................ 502/86

*Primary Examiner*—Carl F. Dees
*Attorney, Agent, or Firm*—Lawrence Rosen

[57] ABSTRACT

An aluminosilicate catalyst for catalytic dehydration of alcohols into ether is prepared by the steps of (a) contacting a crystalline aluminosilicate at below 800° C., preferably 320°–800° C., with a nitrogen-containing base, preferably ammonia or a lower alkyl amine such as n-butyl amine, to absorb as much as possible of the base; and (b) desorbing part of the absorbed base by passing a stream of an inert gas over the thus-treated aluminosilicate at a temperature of 320°–800° C., preferably 400°–600° C. In step (a) the aluminosilicate catalyst is deactivated and in step (b) it is selectively reactivated so that the catalyst catalyses the ether formation reaction almost as well as the untreated catalyst, whereas the catalytic activity for other reactions such as formation of hydrocarbons and formation of "coke" consisting of polymerizates and/or carbon is eliminated. Suitable aluminosilicates to be treated according to the invention are zeolites, notably zeolite H-ZSM-5 and Y-zeolite, and smectites, notably cross-linked natural smectites.

13 Claims, No Drawings

PROCESS FOR THE PREPARATION OF CATALYSTS FOR USE IN ETHER SYNTHESIS

FIELD OF THE INVENTION

The present invention relates to a process for the preparation of aluminosilicate catalysts for use in ether synthesis or processes of which ether synthesis forms part. More specifically, the invention relates to a process for the preparation of such catalysts by the treatment of crystalline aluminosilicates with nitrogen-containing bases.

BACKGROUND OF THE INVENTION

Several caralysts having activity for the catalytic conversion of alcohols into ethers are known, the so called acidic dehydration catalysts. As examples of known acidic dehydration catalysts alumina, e.g. γ-alumina, silica, alumina-silica mixtures and crystalline aluminosilicates, e.g. zeolites and smectites may be mentioned. A common feature of the majority of known acidic dehydration catalysts having an activity sufficiently high for industrial use is a short life because of rapid deactivation. Another drawback of the majority of known acidic dehydration catalysts is that at the same time they catalyze side reactions, resulting in an undesired high content of by-products in the ethers prepared.

The preparation of ethers from alcohols is carried out at elevated pressure and elevated temperature in the presence of the said acidic dehydration catalysts and it proceeds according to the general reaction scheme:

$$R^1OH + R^2OH \rightarrow R^1OR^2 + H_2O \tag{1}$$

wherein $R^1$ and $R^2$ may be like or different and each denote optionally substituted alkyl, aryl or aralkyl groups. However, at the same time as the above desired reaction (1) also undesired side reactions occur, causing, i.a., the formation of hydrocarbons and deactivation of the catalyst employed by depositing so called coke consisting of polymerization products and/or carbon. A content of hydrocarbons in the ethers prepared in itself is undesired. The deactivation of the catalyst in consequence of deposition of coke is however much more serious because it is an accelerating process which rapidly requires the catalyst to be replaced or regenerated. Extensive research has been made especially in order to find catalysts having higher selectivity for the ether formation and less tendency to coke-formation, and moreover to determine optimum process conditions. So far as the crystalline aluminosilicates are concerned, for example, numerous attempts have been made at bringing about improved properties by varying the pore structure and/or by causing atoms of other elements to form part of the crystal lattice. However, hitherto these attempts have been without much success.

Earlier, numerous experiments have been carried out involving the treatment of various catalysts, i.a. crystalline aluminosilicates, with various reagents, i.a. various nitrogen-containing bases. In these experiments it has been demonstrated that the nitrogenous bases become bonded to (poison) the acidic active sites of the catalysts and thereby extensively block the catalytic activity thereof. It is thus known that treatment of crystalline aluminosilicates with nitrogen-containing bases cause these catalysts, which in the untreated state possess catalytic activity for, i.a. the above reaction (1) to, no longer have this activity or only have it to a low degree. Moreover, it has been demonstrated that the blocking of the active sites with nitrogen-containing bases proceed to a high degree of completeness. The treatment of catalysts containing acidic active sites with for example ammonia therefore has also been utilized in the analytical chemistry because the amount of for example ammonia absorbed permits a rather exact determination of the number of acidic active sites of the catalyst in question (N. Topsøe, K. Pedersen, E. G. Derouane, J. Catal. 70, 41-52 (1981)).

It has now been found that by a special treatment of crystalline aluminosilicates known as catalysts it is possible to impart to these a lower deactivation rate and hence a longer life, and at the same time by using such catalysts to obtain a reaction product having a lower content of by-products.

More specifically, it has surprisingly been found that it is possible to effect a partial blocking of the active sites in crystalline aluminosilicates with nitrogen-containing bases whereby there is obtained a selective blocking of various acidic active sites in the catalyst. Thus, mainly a blocking of those active sites that are responsible for the formation of hydrocarbons takes place, whereas the active sites that catalyse ether formation according to the above reaction (1) are blocked to a far lesser extent.

BRIEF DESCRIPTION OF THE INVENTION

According to the invention an aluminosilicate catalyst for use in the catalytic dehydration of alcohols into ethers is prepared by the steps of
(a) contacting a crystalline aluminosilicate at a temperature below 800° C., preferably at 320°-800° C., with one or more nitrogen-containing bases until maximum possible absorption thereof has taken place, and then
(b) subjecting the crystalline aluminosilicate thus treated to an after-treatment consisting in passing a stream of an inert gas over it at a temperature of 320°-800° C., preferably 400°-600° C., to desorb part of the absorbed nitrogen-containing base or bases, this after-treatment being continued until desorption no longer takes place.

DETAILED DESCRIPTION OF THE INVENTION

The treatment of the crystalline aluminosilicate may be carried out by contacting it with one or more nitrogen-containing bases or one or more solutions or dilutions thereof at a temperature of 320°-800° C., or at a lower temperature followed by a heating to 320°-800° C. The needed treatment period depends on the kind of crystalline aluminosilicate, the kind and concentration of nitrogen-containing base or bases employed, the temperature and the pressure employed. The pressure may for instance be from 1 to 100 bar and is unimportant apart from its influence on the treatment period. Useful nitrogen-containing bases generally include those the molecular magnitude of which permit penetration into the pore system of the crystalline aluminosilicate, notably ammonia and lower alkylamines such as alkylamines containing 1-6 carbon atoms in the molecule. The nitrogen-containing bases may be used in the pure form or in the form of liquid solutions, but are however preferably used as gaseous dilutions, e.g. containing from about 0.5 to 10 mol % of base. As solvents low molecular weight inert inorganic or organic solvents may be used, e.g. water. As gaseous diluents low molecular weight inorganic or organic compounds which are inert in the reaction gaseous at the temperature and pressure employed may be used, e.g. nitrogen or hydrogen.

The treatment with nitrogen-containing base is followed by an after-treatment in which the treated crystalline aluminosilicate is scrubbed by a stream of an inert gas being passed over it. In case the treatment has been carried out at a temperature within the range of 320° to 800° C., the after-treatment is likewise carried out at a temperature within this range. In case the treatment has been carried out at a temperature below 320° C., the after-treatment is carried out at a temperature within the range of 320°-800° C.

The concentration of the nitrogen-containing base used for the treatment is not critical because the fact of the matter is that a high concentration permits a short period of treatment but at the same requires a comparatively prolonged scrubbing with inert gas whereas a low concentration calls for a long period of treatment but at the same time permits a comparatively short period of scrubbing.

As will be understood, the critical treatment parameter is the temperature at which the after-treatment is concluded.

The choice of the treatment temperature within the range of 320°-800° C. depends on the desired catalyst properties. A low treatment temperature thus gives a low rate of deactivation and a comparatively low activity for ether formation, whereas a high treatment temperature gives a higher rate of deactivation but at the same time a higher activity for ether formation. In practice it has been found that a treatment temperature within the range of 400°-600° C. in the majority of the cases will provide a catalyst having the desired properties.

The treatment according to the invention described above provides a catalyst having an almost unaltered activity for ether formation but having a strongly reduced activity for hydrocarbon formation and a strongly reduced rate of deactivation.

The favourable effect of the treatment is unexpected on the background of prior art since one could not expect that a partial blocking of the active sites of a crystalline aluminosilicate at the same time would result in a catalyst having increased selectivity for the desired reactions. In other words: it would not be expected that the desorption of the nitrogen-containing base would be selective in the sense that it would result in a selective de-blocking of sites precizely active in the ether formation catalysis.

As mentioned it is known that the treatment of a crystalline aluminosilicate with a nitrogen-containing base, e.g. ammonia, at a lower temperature will result in a blocking of the active sites of the catalyst, imparting also a decrease of the activity of the catalyst for ether formation which is so substantial that in practice the catalyst will be useless for that purpose. It is therefore surprising that it is possible in accordance with the invention to carry out the treatment with a base at a low temperature, e.g. at room temperature, to practically completely block the active sites of the catalyst and thereafter to reestablish the activity specifically, selectively for ether formation of the catalyst by a subsequent heating to a temperature of 320°-800° C.

A suitable crystalline aluminosilicate catalyst to be treated according to the process of the present invention comprises zeolites and layered clay minerals, the so called smectites.

A very useful catalyst based on a synthetic zeolite and made in accordance with the present invention is obtained from the zeolite ZSM-5 which is described detailedly in U.S. Pat. No. 3,702,886. In the examples of the present specification this zeolite is mentioned under the name H-ZSM-5, which means that it is in the hydrogen form. U.S. Pat. No. 3,702,886 does explain in column 2 that such exchange of its normal metal component with hydrogen may take place.

Another synthetic zeolite which will give a very useful ether synthesis catalyst is that known as Y-zeolite.

Also smectites, especially crosslinked natural smectites, may provide very useful catalysts for converting alcohols into ethers. A preferred crosslinked smectite can be prepared by crosslinking a montmorilonnite according to U.S. Pat. No. 3,798,177. This catalyst was used in the experiments described in Example 8 of the present specification.

The catalysts prepared by the process according to the invention as mentioned are useful for the preparation of ethers from alcohols.

Because of the low deactivation tendency of the catalyst it is possible to carry out the conversion of alcohols into ethers at a higher ultimate temperature than possible when using conventional catalysts. The higher ultimate temperature is advantageous because it permits the utilization of the heat of reaction for producing high pressure steam.

In certain cases it will be advantageous, however, to integrate a process for the preparation of an alcohol with a process for the further conversion of that alcohol into an ether. As an example of an advantageous use of such an integration may be mentioned the preparation of synthetic hydrocarbons (e.g. gasoline) from fossil raw materials. The preparation is carried out by a series of process steps one of which is the conversion of a synthesis gas containing carbon oxides and hydrogen into methanol (MeOH), and another may be the conversion of this methanol into dimethyl ether (DME). These two steps proceed according to the reaction schemes:

$$CO + 2H_2 \rightarrow CH_3OH \tag{2}$$

$$2CH_3OH \rightarrow CH_3OCH_3 + H_2O \tag{3}$$

an equilibrium simultaneously establishing itself according to the shift reaction:

$$CO + H_2O \rightleftharpoons CO_2 + H_2O \tag{4}$$

It has been shown in U.S. Pat. No. 4,481,305 that it may be advantageous to carry out the reactions (2), (3) and (4) in one and the same reactor in the presence of suitable catalysts. As examples of known catalysts for reactions (2) and (4) may be mentioned oxides of zinc and chromium, oxides of zinc and aluminium, oxides of copper, chromium and zinc or oxides of copper, zinc and aluminium. The metal oxides mentioned may be used as a physical mixture, or one can use complex oxides where the two or three oxides are chemically and/or physically combined in one oxidic structure. Examples of known catalysts for reaction (3) are mentioned hereinbefore. By using a catalyst according to the present invention for reaction (3), however, considerable advantages are obtained as will appear from the foregoing.

The catalysts may be used in the form of a mixture of particles containing a catalyst having activity for reactions (2) and (4) and particles containing a catalyst according to the present invention having activity for reaction (3), or they may be used in the form of particles each containing both of the catalyst types.

In the following the invention will be further illustrated by the aid of examples.

EXAMPLE 1

Zeolite H-ZSM-5 (3 g) was calcined (to remove any moisture) in a glass reactor for 1 hour at 550° C. in a stream of pure $N_2$ at atmospheric pressure. Thereafter the temperature in the glass reactor was adjusted to 250° C., the $NH_3$ treatment temperature. At this temperature and atmospheric pressure a stream of $N_2$ containing 0.5% by volume of $NH_3$ was admitted. This treatment was continued for ½ hour after the concentration of $NH_3$ in the exit stream had reached 0.5% by volume. Then the addition of $NH_3$ was discontinued and the reactor system scrubbed with pure $N_2$ at the same temperature and pressure until $NH_3$ could no longer be detected in the discharge system. Thereafter the reactor was cooled to room temperature. The process described in the present Example was repeated on 10 further H-ZSM-5 samples, yet in a manner so as to vary the $NH_3$ treatment temperature from 275° to 650° C.

After the treatment all of the catalysts were analyzed with respect to content of $NH_3$. These analysis results are shown in Table 1. In this and in the following the concentrations are given in p.p.m. by weight.

TABLE 1

| Treatment Temperature °C. | Content of $NH_3$ p.p.m. |
|---|---|
| 250 | 3860 |
| 275 | 2850 |
| 300 | 2820 |
| 325 | 1590 |
| 350 | 955 |
| 400 | 795 |
| 450 | 620 |
| 500 | 535 |
| 550 | 260 |
| 600 | 245 |
| 650 | 185 |

EXAMPLE 2

Zeolite H-ZSM-5 (3 g) was calcined in a glass reactor for 1 hour at 550° C. in a stream of pure $N_2$ at atmospheric pressure.

The DME catalyst thereby obtained was mixed with a copper-based MeOH catalyst to a weight ratio of 1:1. The catalyst mixture was placed in a microreactor having an internal diameter of 10 mm. After reduction of the MeOH catalyst it was tested under the following conditions:
Pressure: 60 kg/cm²g
Temperature: 280° C. isothermally
Flow: 5.5 Nl/h/g catalyst
Feed gas: a mixture of 5.0% by vol. CO, 3.5% by vol. $CO_2$, 3.0% by vol. Ar. 88.5% by vol. $H_2$
The experimental results are shown in Table 2.

TABLE 2

| Time h | Conversion of CO + $CO_2$ % | Distance to MeOH equilibrium °C. | DME % vol. |
|---|---|---|---|
| 30 | 51.8 | 1 | 2.9 |
| 239 | 38.4 | 33 | 2.0 |
| 355 | 31.0 | 58 | 1.3 |
| 509 | 26.2 | 65 | 1.1 |

The following applies to Table 2 and the corresponding Tables hereinbelow:

The first column shows the number of hours elapsed from the start of the experiment.

The second column shows the proportion of the total content of CO and $CO_2$ that is converted during the passage of the reactor.

The third column shows the distance to MeOH equilibrium, i.e. equilibrium temperature corresponding to the gas composition after passage through the reactor minus the actual temperature.

The fourth column shows the content of DME in the converted gas.

EXAMPLE 3

Zeolite H-ZSM-5 (3500 g) was placed in a tubular reactor having an inner diameter of 100 mm. The catalyst was heated to 540° C. in a stream of pure $N_2$ at atmospheric pressure. At the same temperature and pressure $NH_3$ was added to the stream of $N_2$ so as to give the stream a content of about 2% by vol. of $NH_3$. This treatment was continued for ½ hour after the concentration of $NH_3$ in the exit stream had reached 2%. Then the addition of $NH_3$ was discontinued and the reactor system scrubbed with $N_2$ at the same temperature and pressure until $NH_3$ could no longer be detected in the discharge system. After this the catalyst was cooled to room temperature. The content of $NH_3$ in the zeolite was analyzed to be 545 p.p.m. The DME catalyst thereby prepared was mixed with a copper based MeOH catalyst to the weight ratio 2:3. The catalyst mixture was placed in a reactor system as in Example 2 and tested at the same conditions. The experimental results are shown in Table 3.

TABLE 3

| Time h | Conversion of CO + $CO_2$ % | Distance to MeOH equilibrium °C. | DME % vol. |
|---|---|---|---|
| 52 | 71.3 | −5 | 2.9 |
| 296 | 68.6 | −6 | 2.8 |
| 437 | 68.1 | −2 | 2.8 |
| 725 | 68.1 | −3 | 2.7 |

EXAMPLE 4

Zeolite H-ZSM-5 (3 g) was treated as in Example 1 at a $NH_3$ treatment temperature of 525° C. The DME catalyst thereby prepared was mixed with a copper-based MeOH catalyst to the weight ratio 1:1. The catalyst mixture was tested as in Example 2. The experimental results are shown in Table 4.

TABLE 4

| Time h | Conversion of CO + $CO_2$ % | Distance to MeOH equilibrium °C. | DME % vol. |
|---|---|---|---|
| 19 | 69.2 | −7 | 3.1 |
| 202 | 67.2 | −3 | 2.9 |

TABLE 4-continued

| Time h | Conversion of CO + CO$_2$ % | Distance to MeOH equilibrium °C. | DME % vol. |
|---|---|---|---|
| 409 | 68.5 | −1 | 2.7 |

EXAMPLE 5

Zeolite H-ZSM-5 (1.5 g) was heated in a glass reactor to 500° C. in a stream of dry H$_2$. the temperature was maintained for 1 hour after which the catalyst was cooled to room temperature, still in a stream of dry H$_2$. At room temperature the stream was saturated with n-butyl amine. Altogether 0.5 ml of n-butyl amine was added. When the wxit stream was free of n-butylamine the catalyst was heated in a stream of dry H$_2$ to 250° C. (the after-treatment temperature) which was maintained for ½ hour. Thereafter the catalyst was cooled. After the treatment the content of N in the zeolite was analyzed to be 4200 p.p.m. of N. The content in the untreated zeolite was analyzed to be 100 p.p.m. of N. The DME catalyst thus prepared was mixed with a MeOH catalyst to the weight proportion 40:60. The catalyst was tested in the same manner as in Example 2. The experimental results are shown in Table 5.

TABLE 5

| Time h | Conversion of CO + CO$_2$ % | Distance to MeOH equilibrium °C. | DME % vol. |
|---|---|---|---|
| 3 | 65.5 | −5 | 2.5 |
| 103 | 61.3 | −2 | 2.1 |
| 246 | 60.4 | −3 | 2.0 |
| 416 | 58.9 | −2 | 1.8 |
| 605 | 56.3 | −1 | 1.6 |

EXAMPLE 6

Zeolite H-ZSM-5 (1.5 g) was treated in the same way as in Example 5, the after-treatment temperature however being 500° C.

After the treatment the content of N in the zeolite was analyzed to be 1330 p.p.m. of N. The content of N in the untreated zeolite was analyzed to be 100 p.p.m. of N. The DME catalyst thus prepared was mixed with a MeOH catalyst to the weight proportion of 40:60. The catalyst was tested in the same manner as in Example 2. The experimental results are shown in Table 6.

TABLE 6

| Time h | Conversion of CO + CO$_2$ % | Distance to MeOH equilibrium °C. | DME % vol. |
|---|---|---|---|
| 5 | 69.2 | −7 | 2.9 |
| 159 | 67.6 | 0 | 2.7 |
| 603 | 67.7 | −1 | 2.5 |
| 940 | 65.5 | 5 | 2.5 |

EXAMPLE 7

Y-zeolite (10 g) was treated in the same manner as the zeolite H-ZSM-5 according to Example 3. The content of NH$_3$ in the zeolite was analyzed to be 1890 p.p.m. of NH$_3$ The DME catalyst thus prepared was mixed with a MeOH catalyst to a ratio of 1.1. The catalyst was tested in the same manner as in Example 2. The experimental results are shown in Table 7.

TABLE 7

| Time h | Conversion of CO + CO$_2$ % | Distance to MeOH equilibrium °C. | DME % vol. |
|---|---|---|---|
| 17 | 68.6 | −6 | 2.7 |
| 250 | 65.5 | 1 | 2.5 |
| 358 | 66.6 | −1 | 2.7 |
| 484 | 65.0 | 3 | 2.6 |
| 894 | 59.4 | 11 | 2.3 |

EXAMPLE 8

Smectite (10 g) in the H form was treated in the same manner as the zeolite H-ZSM-5 according to Example 3. The DME catalyst thereby prepared was mixed with a MeOH catalyst to the weight ratio 60:40. The catalyst was tested as in Example 2. The experimental results are shown in Table 8.

TABLE 8

| Time h | Conversion of CO + CO$_2$ % | Distance to MeOH equilibrium °C. | DME % vol. |
|---|---|---|---|
| 6 | 67.8 | −5 | 2.6 |
| 154 | 58.3 | −4 | 1.6 |
| 322 | 58.7 | −5 | 1.6 |
| 581 | 57.9 | −6 | 1.6 |

Example 1 shows how the absorbed amount of NH$_3$ depends on the temperature.

Example 2 is a comparison Example which shows how fast untreated H-ZSM-5 deactivates.

Examples 3 and 4 show the low rate of deactivation of H-ZSM-5 treated with NH$_3$, partly in pilot scale and partly in laboratory scale.

Examples 5 and 6 show the treatment of H-ZSM-5 with n-butyl amine as well as the influence of the after-treatment temperature on the properties of the catalyst obtained.

Example 7 shows the results obtained by treatment with another type of zeolite, Y-zeolite.

Example 8 shows the results obtained by the treatment of a smectite.

I claim:

1. A process for the preparation of an aluminosilicate catalyst for use in the catalytic dehydration of alcohols into ethers, wherein the improvement consists in the steps of
   (a) contacting a crystalline aluminosilicate at a temperature below 800° C. with at least one nitrogen-containing base and carrying out this treatment until no more of such base is absorbed, and then
   (b) subjecting the crystalline aluminosilicate thus treated to an after-treatment consisting in passing a stream of an inert gas over it at a temperature of 320°–800° C. to desorb part of any nitrogen-containing base absorbed, this after-treatment being carried out until desorption no longer takes place.

2. The process claimed in claim 1, wherein the nitrogen-containing base employed is ammonia.

3. The process claimed in claim 1, wherein the nitrogen-containing base employed is at least one lower alkyl amine.

4. The process claimed in claim 3, wherein the nitrogen-containing base employed is n-butyl amine.

5. The process claimed in claim 1, wherein the crystalline aluminosilicate is a zeolite.

6. The process claimed in claim 5, wherein the zeolite is zeolite -H-ZSM-5.

7. The process claimed in claim 5, wherein the zeolite is Y-zeolite.

8. The process claimed in claim 1, wherein the crystalline aluminosilicate is a smectite.

9. The process claimed in claim 8, wherein the smectite is a crosslinked natural smectite.

10. The process claimed in claim 1, wherein the absorption step (a) is carried out at a temperature of 320°–800° C.

11. The process claimed in claim 1, wherein the desorption step (b) is carried out at a temperature of 400°–600° C.

12. The process claimed in claim 1 wherein the absorption step (a) is carried out at atmospheric pressure.

13. The process claimed in claim 1, wherein the desorption step (b) is carried out at atmospheric pressure.

* * * * *